United States Patent
Benser et al.

(10) Patent No.: US 7,899,531 B1
(45) Date of Patent: Mar. 1, 2011

(54) NEURAL SENSING FOR ATRIAL FIBRILLATION

(75) Inventors: Michael Benser, Valencia, CA (US); Taraneh Ghaffari Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 303 days.

(21) Appl. No.: 11/466,418

(22) Filed: Aug. 22, 2006

(51) Int. Cl.
*A61N 1/00* (2006.01)
*A61B 5/02* (2006.01)

(52) U.S. Cl. ............... 607/6; 607/5; 607/9; 607/18; 600/483

(58) Field of Classification Search ............ 607/5–6, 607/9, 18; 600/483
See application file for complete search history.

(56) References Cited

U.S. PATENT DOCUMENTS

| | | | |
|---|---|---|---|
| 5,366,487 A * | 11/1994 | Adams et al. ............... | 607/5 |
| 5,385,576 A * | 1/1995 | Noren et al. ................ | 607/6 |
| 5,464,434 A * | 11/1995 | Alt .............................. | 607/6 |
| 5,522,854 A * | 6/1996 | Ideker et al. ................ | 607/6 |
| 5,658,318 A | 8/1997 | Stroetmann et al. | |
| 5,974,340 A * | 10/1999 | Kadhiresan ................ | 607/18 |
| 6,266,563 B1 * | 7/2001 | KenKnight et al. ......... | 607/5 |
| 6,393,316 B1 * | 5/2002 | Gillberg et al. ............ | 600/515 |
| 6,405,082 B1 * | 6/2002 | Borgenicht ................ | 607/5 |
| 6,473,644 B1 * | 10/2002 | Terry et al. ................ | 607/2 |
| 7,123,961 B1 * | 10/2006 | Kroll et al. ................. | 607/9 |
| 2004/0193231 A1 * | 9/2004 | David et al. ................ | 607/48 |
| 2004/0199210 A1 * | 10/2004 | Shelchuk .................. | 607/17 |
| 2005/0187586 A1 * | 8/2005 | David et al. ............... | 607/9 |
| 2006/0206155 A1 * | 9/2006 | Ben-David et al. ......... | 607/9 |
| 2006/0206159 A1 * | 9/2006 | Moffitt et al. .............. | 607/37 |

FOREIGN PATENT DOCUMENTS

| | | | |
|---|---|---|---|
| EP | 588127 A1 * | 3/1994 | |
| EP | 0688578 B1 | 11/1999 | |
| GB | 2216266 A * | 10/1989 | |
| JP | 04071532 A * | 3/1992 | |

OTHER PUBLICATIONS

Kawashima, Tomokazu, "The autonomic nervous system of the human heart with special reference to its origin, course, and peripheral distribution," Anat Embryol (2005) 209; 425-438.
Jones, James F.X., "Vagal control of the rat heart," (Physiologal Society Symposium—Vagal Control: From Axolotl to Man), Exp. Physiol 2001;86;797-801.

* cited by examiner

*Primary Examiner* — Niketa I Patel
*Assistant Examiner* — Nicole F Lavert

(57) ABSTRACT

An exemplary method includes acquiring patient activity information and/or nerve activity information, detecting one or more episodes of atrial fibrillation, associating the information with atrial fibrillation and, upon occurrence of particular patient activity and/or nerve activity, calling for delivery of an anti-atrial fibrillation therapy. Various other exemplary methods, devices, systems, etc., are also disclosed.

10 Claims, 7 Drawing Sheets

NEURAL SENSING FOR ATRIAL FIBRILLATION

FIELD OF THE INVENTION

Exemplary techniques presented herein generally relate to autonomic nerve activity and/or patient activity and associating such activities with respect to atrial arrhythmias. Various exemplary techniques may be used with cardiac pacing therapy and/or anti-arrhythmia therapy.

BACKGROUND

The autonomic nervous system and the cardiovascular system are highly integrated whereby a change to one system generally affects the other system. The autonomic nervous system extends across the body and affects the cardiovascular system through both intracardiac and extracardiac mechanisms. For example, arterial baroreceptors may be considered part of an extracardiac parasympathetic mechanism while cardiac ganglia may be considered part of intracardiac parasympathetic and sympathetic mechanisms.

With respect to intracardiac mechanisms, various studies indicate that electrical, mechanical or chemical stimulation of epicardial "fat pads" can have a profound affect on the cardiovascular system. These so called "fat pads" may be more appropriately described as neural plexuses or subplexuses that are highly innervated with parasympathetic and sympathetic nerves. However, correspondence is not straightforward between autonomic pathways and cardiac behavior. For example, uncertainty exists as to on-set of arrhythmias and autonomic nerve activity or a lack thereof. Various exemplary methods, devices, systems, etc., described herein aim to understand better the relationship between autonomic pathways and atrial arrhythmias and to use such understanding for delivery of anti-arrhythmia therapies.

SUMMARY

An exemplary method includes acquiring patient activity information and/or nerve activity information, detecting one or more episodes of atrial fibrillation, associating the information with atrial fibrillation and, upon occurrence of particular patient activity and/or nerve activity, calling for delivery of an anti-atrial fibrillation therapy. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

An exemplary sensing and stimulation device is described followed by a description of the cardiovascular system. The description of autonomic nerve physiology includes relationships to cardiac plexuses and subplexuses. Various exemplary electrode configurations are described followed by a discussion of exemplary controllers, control logic and methods that pertain generally to prevention and termination of atrial arrhythmias.

Exemplary Device

The techniques described below are intended to be implemented in connection with any stimulation device that is configured or configurable to sense and stimulate nerves and/or tissue, including stimulation of a patient's heart. While various examples refer to an implantable device, other examples are optionally implemented using an external device or a combination of internal and external components. For example, with respect to external devices, autonomic nerve activation has been achieved using external devices that deliver electromagnetic or magnetic radiation to a body (e.g., neck region, etc.). In another example, an external device for autonomic nerve activation may communicate with an implanted device (e.g., an implanted cardiac therapy device, etc.).

Figure 1:
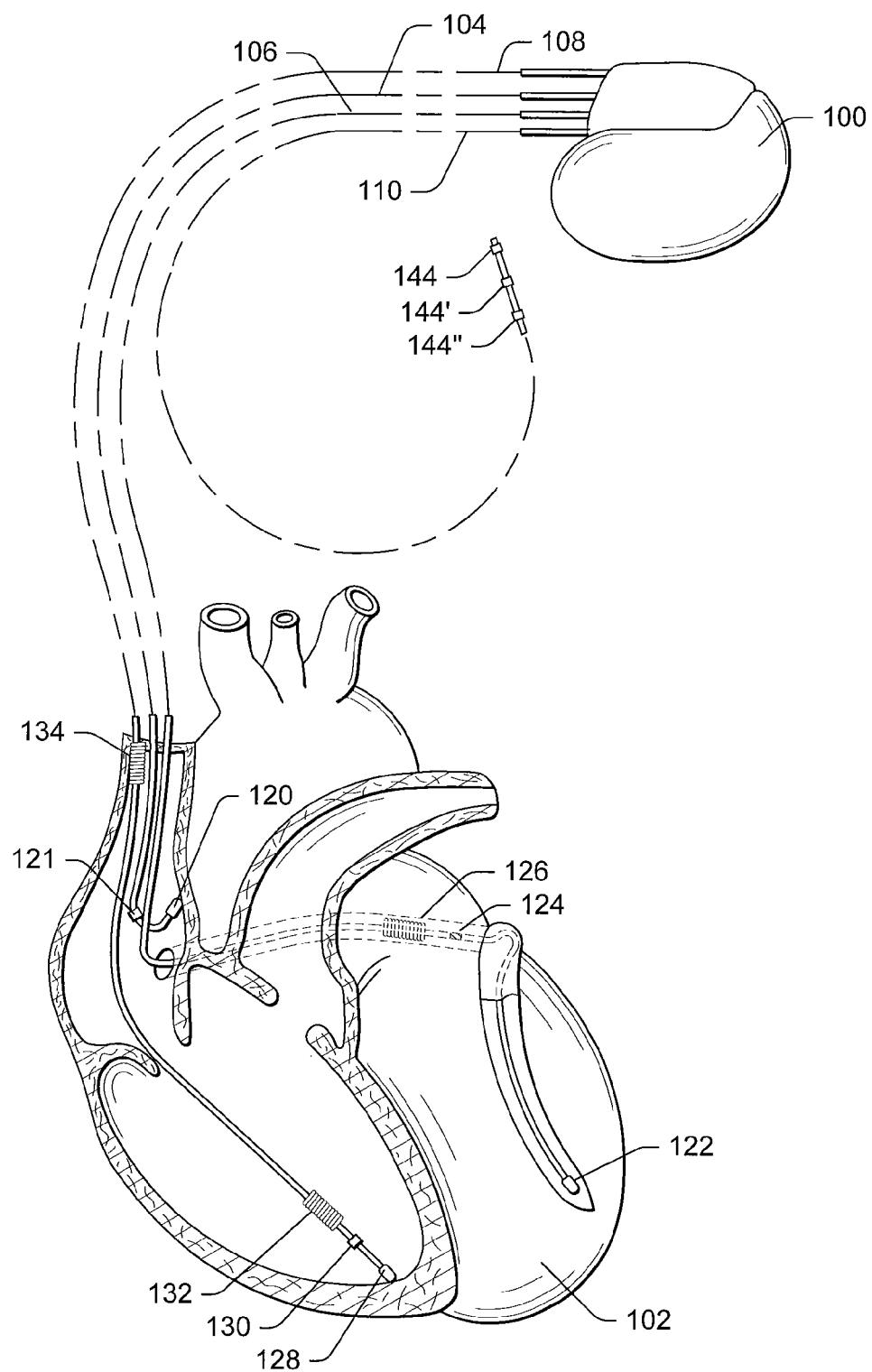
FIG. 1 is a simplified diagram illustrating an exemplary implantable stimulation device in electrical communication with at least three leads implanted into a patient's heart and at least one other lead for sensing or delivering stimulation or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves and/or for sensing autonomic nerve activity. In such configurations, the number of electrodes may vary from the number shown; electrode type may vary as well.

The device 100 includes a fourth lead 110 having, in this implementation, three electrodes 144, 144', 144" suitable for stimulation of tissue such as autonomic nerves and/or sensing physiologic signals (e.g., autonomic nerve activity) that may be used by the implanted system to modify therapy parameters. Such a lead is optional as a suitable device may have more or few leads than the device 100 shown in FIG. 1. The lead 110 may be positioned in and/or near a patient's heart or within a patient's body and remote from the heart.

The right atrial lead 104, as the name implies, is positioned in and/or passes through a patient's right atrium. The right atrial lead 104 may be used for sensing atrial cardiac signals, for providing right atrial chamber stimulation therapy and optionally for sensing autonomic nerve activity. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves or other tissue or for sensing activity of autonomic nerves or other tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 may be used to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 may be used to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of an example of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 may further include electrodes for stimulation of autonomic nerves or for sensing autonomic nerve activity. For example, an exemplary coronary sinus lead includes pacing electrodes capable of delivering pacing pulses to a patient's left ventricle and at least one electrode capable of stimulating an autonomic nerve and/or sensing activity of an autonomic nerve. An exemplary coronary sinus lead (or left ventricular lead or left atrial lead) may also include at least one electrode on a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve and/or sensing activity of an autonomic nerve. Such an electrode may be positioned on the lead or a bifurcation or leg of the lead.

As already mentioned, more than one device may be used for performing various exemplary method described herein. For example, one device may operate to sense autonomic nerve activity while another device operates to delivery myocardial stimulation. In such an example, communication may occur from one device to the other or bi-directionally between the two devices. Communication may occur via telemetric circuit or by a circuit that emits energy into body tissue, at least some of the emitted energy receivable or detectable by the other device.

Figure 2:
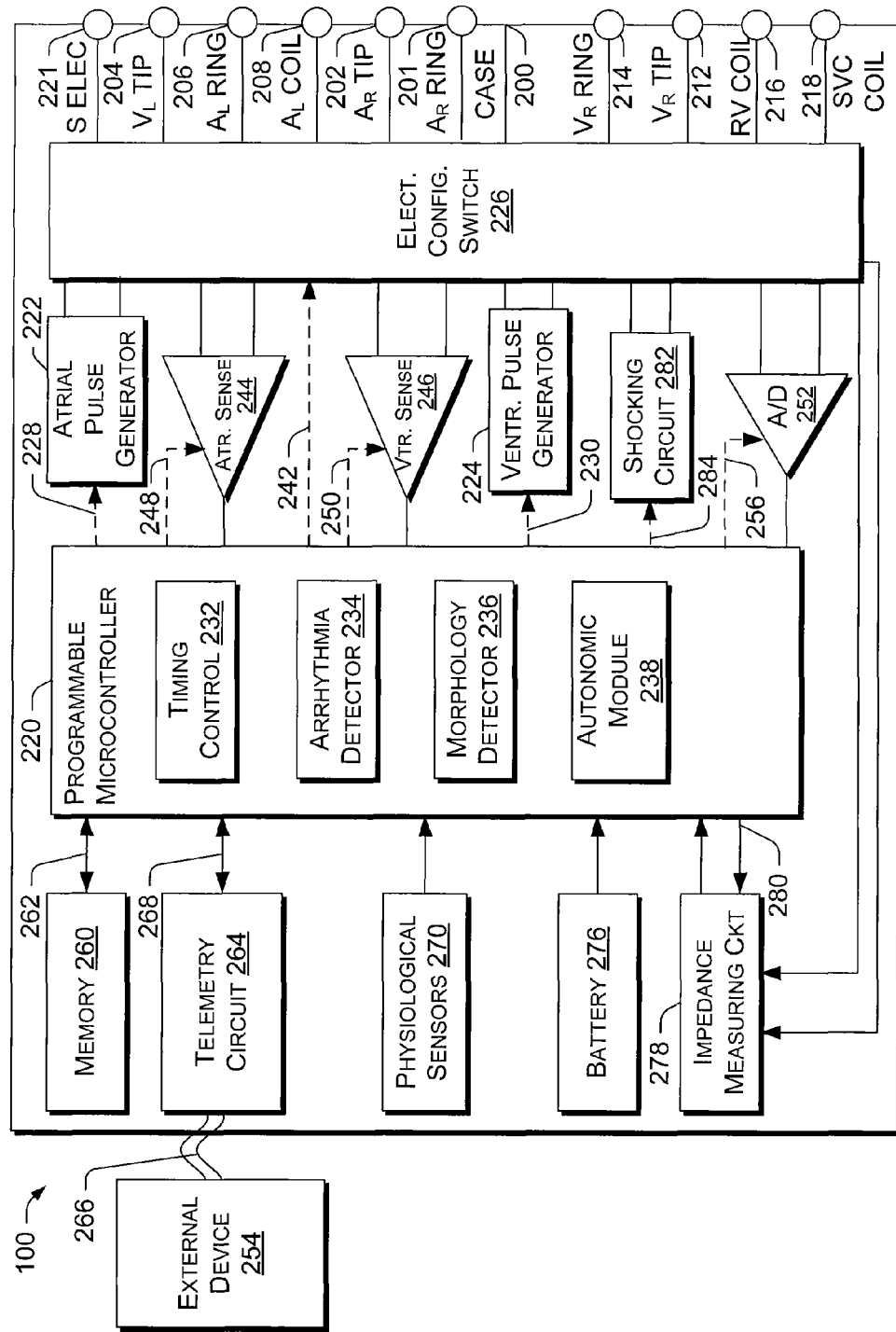
FIG. 2 is a functional block diagram of an exemplary implantable stimulation device illustrating basic elements that are configured to provide cardioversion, defibrillation, pacing stimulation or autonomic nerve stimulation or other tissue or nerve stimulation. The implantable stimulation device is further configured to sense information and administer stimulation pulses responsive to such information.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. As described in more detail below, delivery of atrial anti-arrhythmia therapy may occur in response to classification of autonomic nerve activity.

While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing, autonomic nerve stimulation and/or autonomic nerve sensing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121.

To achieve left chamber sensing, pacing, shocking, autonomic nerve stimulation and/or autonomic nerve sensing, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to other suitable tissue stimulation electrodes is also possible via these and/or other terminals (e.g., via a stimulation/sensing terminal S ELEC 221). In general, the stimulation/sensing terminal S ELEC 221 may be used for any of a variety of tissue activation or tissue sensing. An exemplary device may include one or more such terminals for purposes of stimulation and/or sensing.

To support right chamber sensing, pacing, shocking, autonomic nerve stimulation and/or autonomic nerve sensing, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of various therapies, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or for other tissue activation) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234 and optionally an orthostatic compensator and/or a minute ventilation (MV) response module, the latter are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a morphology discrimination module 236. This module is optionally used to implement various exemplary recognition algorithms. For example, the module 236 may include algorithms for recognition of certain characteristics in autonomic nerve activity, as described in more detail below. The aforementioned components may be implemented in hardware as part of the microcontroller 220, or as software/firmware instructions programmed into the device and executed on the microcontroller 220 during certain modes of operation.

Microcontroller 220 further includes an autonomic module 238 for performing a variety of tasks related to autonomic nerve sensing and/or stimulation. This component may also be utilized by the device 100 for determining desirable times to administer various therapies (e.g., atrial anti-arrhythmia therapies). The module 238 may be implemented in hardware as part of the microcontroller 220 or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art. Similarly, the switch 226 may configure or select electrodes for sensing.

Atrial sensing circuits 244 and ventricular sensing circuits 246 may also be selectively coupled to the right atrial lead 104, coronary sinus lead 106, the right ventricular lead 108, and the lead 110 through the switch 226 for any of a variety of purposes (e.g., detecting the presence of cardiac activity in each of the four chambers of the heart, sensing autonomic nerve activity, etc.). Accordingly, the atrial (ATR. SENSE) and ventricular (VTR. SENSE) sensing circuits, 244 and 246, may include dedicated sense amplifiers, multiplexed amplifiers, or shared amplifiers. Switch 226 can determine the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac or autonomic nerve signal of interest. The automatic gain control enables the device 100 to deal effectively with the difficult problem of sensing the low amplitude signal characteristics of atrial or ventricular fibrillation. Such gain control may aid in sensing of other signals (e.g., autonomic nerve, etc.).

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia. Various exemplary techniques described herein pertain to classification of autonomic nerve activity with respect to atrial behavior. Such techniques rely on sensed information and can detect or aid in detection of an arrhythmia or of a precursor or other factor that may indicate a risk of or likelihood of an imminent onset of an arrhythmia. Thus, the module 234 may rely, where appropriate, on the autonomic module 238.

Such an exemplary detection module 234, optionally uses timing intervals between sensed events (e.g., P-waves, R-waves, and depolarization signals associated with fibrillation which are sometimes referred to as "F-waves" or "Fibwaves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. Such a module is optionally suitable for performing various exemplary methods described herein. For example, such a module optionally allows for analyses related to action potentials (e.g., MAPs, T waves, etc.) and characteristics thereof (e.g., alternans, activation times, repolarization times, derivatives, etc.).

Cardiac signals and/or other signals are typically applied to inputs of an analog-to-digital (A/D) data acquisition system 252. For example, the data acquisition system 252 can be configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the lead 110 lead through the switch 226 to sample cardiac signals or other signals across any pair of desired electrodes. Programmable control of the data acquisition system 252 by the programmable controller 220 can be achieved via the signal line 256.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms, status information and/or other information relating to the operation of the device 100 (as contained in the microcontroller 220 or memory 260) to be sent to the external device 254 through an established communication link 266.

The stimulation device 100 can further includes one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

Various exemplary methods, devices, systems, etc., described herein optionally use such a pressure transducer to measure pressures in the body (e.g., chamber of heart, vessel, etc.). The company, Radi Medical Systems AB (Uppsala, Sweden), markets various lead-based sensors for intracoronary pressure measurements, coronary flow reserve measurements and intravascular temperature measurements. Such sensor technologies may be suitably adapted for use with an implantable device for in vivo measurements of physiology.

The companies Nellcor (Pleasanton, Calif.) and Masimo Corporation (Irvine, Calif.) market pulse oximeters that may be used externally (e.g., finger, toe, etc.). Where desired, information from such external sensors may be communicated wirelessly to the implantable device, for example, via an implantable device programmer. Other sensors may be implantable and suitably connected to or in communication with the exemplary implantable device 100. Technology exists for lead-based oximeters. For example, a study by Tsukada et al., "Development of catheter-type optical oxygen sensor and applications to bioinstrumentation," *Biosens Bioelectron*, 2003 Oct. 15; 18(12):1439-45, reported use of a catheter-type optical oxygen sensor based on phosphorescence lifetime.

Various photoplethysmography techniques suitable for use with an implantable device such as the device 100 are disclosed in U.S. Pat. No. 6,491,639 (Turcott), issued Dec. 10, 2002 and U.S. Pat. No. 6,731,967 (Turcott), issued May 4, 2004, which are incorporated herein by reference. The exemplary implantable device 100 may include or operate in conjunction with one or more PPG sensors in a can-based, lead-based or other manner whereby PPG information is communicated to the device. Such sensors may determine $SaO_2$, $SvO_2$ or other oxygen-related parameters. Other sensors suitable for use with the exemplary device 100 include cardiomechanical sensors (CMEs).

The one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

Further, depending on position of the implanted device and such a movement sensor, the sensor may measure or monitor chest movement indicative of respiratory characteristics. For example, for a typical implant in the upper chest, upon inspiration, the upper chest expands thereby causing the implanted device to move. Accordingly, upon expiration, the contraction of the upper chest causes the device to move again. Such a movement sensor may sense information capable of distinguishing whether a patient is horizontal, vertical, etc.

While respiratory information may be obtained via the one or more physiologic sensors 270, a minute ventilation (MV) sensor may sense respiratory information related to minute ventilation, which is defined as the total volume of air that moves in and out of a patient's lungs in a minute. A typical MV sensor uses thoracic impedance, which is a measure of impedance across the chest cavity wherein lungs filled with air have higher impedance than empty lungs. Thus, upon inhalation, impedance increases; whereas upon exhalation, impedance decreases. Of course, a thoracic impedance (e.g., intrathoracic impedance) may be used to determine tidal volume or measures other than minute ventilation.

With respect to impedance measurement electrode configurations, a right ventricular tip electrode and case electrode may provide current while a right ventricular ring electrode and case electrode may allow for potential sensing. Of course, other configurations and/or arrangements may be used to acquire measurements over other paths (e.g., a superior-inferior path and a left-right path, etc.). Multiple measurements may be used wherein each measurement has a corresponding path.

Direct measurement of autonomic nerve activity (e.g., vagal nerve or sympathetic nerve) may be achieved using a cuff or other suitable electrode appropriately positioned in relationship to an autonomic nerve. Nerve signals are typically of amplitude measured in microvolts (e.g., less than approximately 30 microvolts). Sensing may be coordinated with other events, whether natural event or events related to some form of stimulation therapy. As discussed herein, some degree of synchronization may occur between calling for and/or delivering stimulation for autonomic nerve activation and sensing of neural activity.

Signals generated by the one or more physiologic sensors 270 (e.g., MV sensor, impedance sensor, blood pressure, etc.) are optionally processed by the microcontroller 220 in determining whether to apply one or more therapies. More specifically, with respect to a movement sensor, the microcontroller 220 may receive a signal from an accelerometer-based sensor that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke an orthostatic compensator to apply a prescribed stimulation therapy, especially at the onset. If the patient is traversing downstairs, the device might decrease a pacing rate or perhaps invoke a MV response module (e.g., operational with the microcontroller 220) to control one or more therapies during the descent. The MV response module may provide information to be used in determining a suitable pacing rate by, for example, measuring the thoracic impedance from a MV sensor, computing the current MV, and comparing that with a long-term average of MV.

The microcontroller 220 can also monitor one or more of the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke, for example, an orthostatic compensator to apply cardiac pacing therapy for treating orthostatic hypotension. Other possible uses also exist with respect to autonomic nerve activation for blood pressure control or for other purposes.

While a two-axis accelerometer may adequately detect tilt with respect to acceleration of gravity, the exemplary stimulation device 100 may also or alternatively be equipped with a GMR (giant magnetoresistance) sensor and circuitry that detects the earth's magnetic fields. Such a GMR sensor and circuitry may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of an accelerometer-based sensor might change by 90°, but the sensor signals may be calibrated as to the true vertical direction based on the output of a GMR sensor and circuitry.

The stimulation device additionally includes a battery 276 that provides operating power to all of the circuits shown in FIG. 2. For the stimulation device 100, which can employ shocking therapy, the battery 276 is capable of operating at low current drains for long periods of time (e.g., preferably less than 10 µA), and is capable of providing high-current pulses (for capacitor charging) when the patient requires a shock or other stimulation pulse, for example, according to various exemplary methods, systems and/or devices described below. The battery 276 also desirably has a predictable discharge characteristic so that elective replacement time can be determined a priori or detected.

The stimulation device 100 can further include magnet detection circuitry (not shown in FIG. 2), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The impedance measuring circuit 278 may operate with an impedance sensor included as one of the physiological sensors 270. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within or proximate to the chest cavity. Various exemplary methods described below optionally rely on impedance measurements to determine lung inflation, inspiratory vagal excitation, which can inhibit excitatory signals to various muscles (e.g., diaphragm, external intercostals, etc.), or blood pressure (e.g., via relationship between vessel size due to blood pressure changes, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia and converting the heart back to a normal sinus rhythm. To this end, the microcontroller 220 further controls a shocking circuit 282 by way of a control signal 284. Shocking circuit 282 is presented as an example herein as other exemplary circuits are discussed below for charging and/or discharging stored charge.

In this example, the shocking circuit 282 can generate shocking or stimulation pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), typically delivered synchronously, though R-waves may be disorganized, and pertaining exclusively to the treatment of fibrillation or fast polymorphic VT (e.g., ventricular fibrillation, which is discussed in more detail below). Accordingly, the microcontroller 220 is capable of controlling the synchronous or asynchronous delivery of the shocking pulses.

As already mentioned, the device 100 of FIGS. 1 and 2 has various features suitable for sensing autonomic nerve activity and calling for and delivering energy for myocardial and/or autonomic nerve activation. With respect to autonomic nerves, the module 238 may be used together with any of the various pulse generators, electrodes, etc. In general, autonomic nerve activation involves direct or indirect nerve stimulation and/or transvenous nerve stimulation. Such stimulation may aim to stimulate autonomic nerves distant from the heart or proximate to the heart, including cardiac plexuses or subplexuses. The term plexus includes subplexus.

The description of the device 100 of FIGS. 1 and 2 makes various references to autonomic nerves; however, such a device may be used for other nerve sensing and/or stimulation (CNS, etc.). For example, some afferent autonomic nerves transmit information from the periphery to the CNS. In addition, some afferent autonomic nerves interact with the CNS concerned with the mediation of visceral sensation and the regulation of vasomotor and respiratory reflexes, for example the baroreceptors and chemoreceptors in the carotid sinus and aortic arch which are important in the control of heart rate, blood pressure and respiratory activity. These afferent fibres are usually carried to the CNS by major autonomic nerves such as the vagus, splanchnic or pelvic nerves, although afferent pain nerve fibers from blood vessels may be carried by somatic nerves.

Various exemplary methods, devices, systems, etc., include mechanisms for classifying information carried by autonomic nerves. In particular, an exemplary method may include sensing nerve activity in one or more parasympathetic, cardiac pathways and classifying such activity as associated with one or more types of atrial arrhythmias. An exemplary controller may then call for a particular action based at least in part on a classification of the parasympathetic activity. For example, where parasympathetic nerve activity is classified as being associated with aright atrial arrhythmia, then a controller may call for delivery of anti-arrhythmia therapy to the right atrium. Other examples are discussed below.

Figure 3:
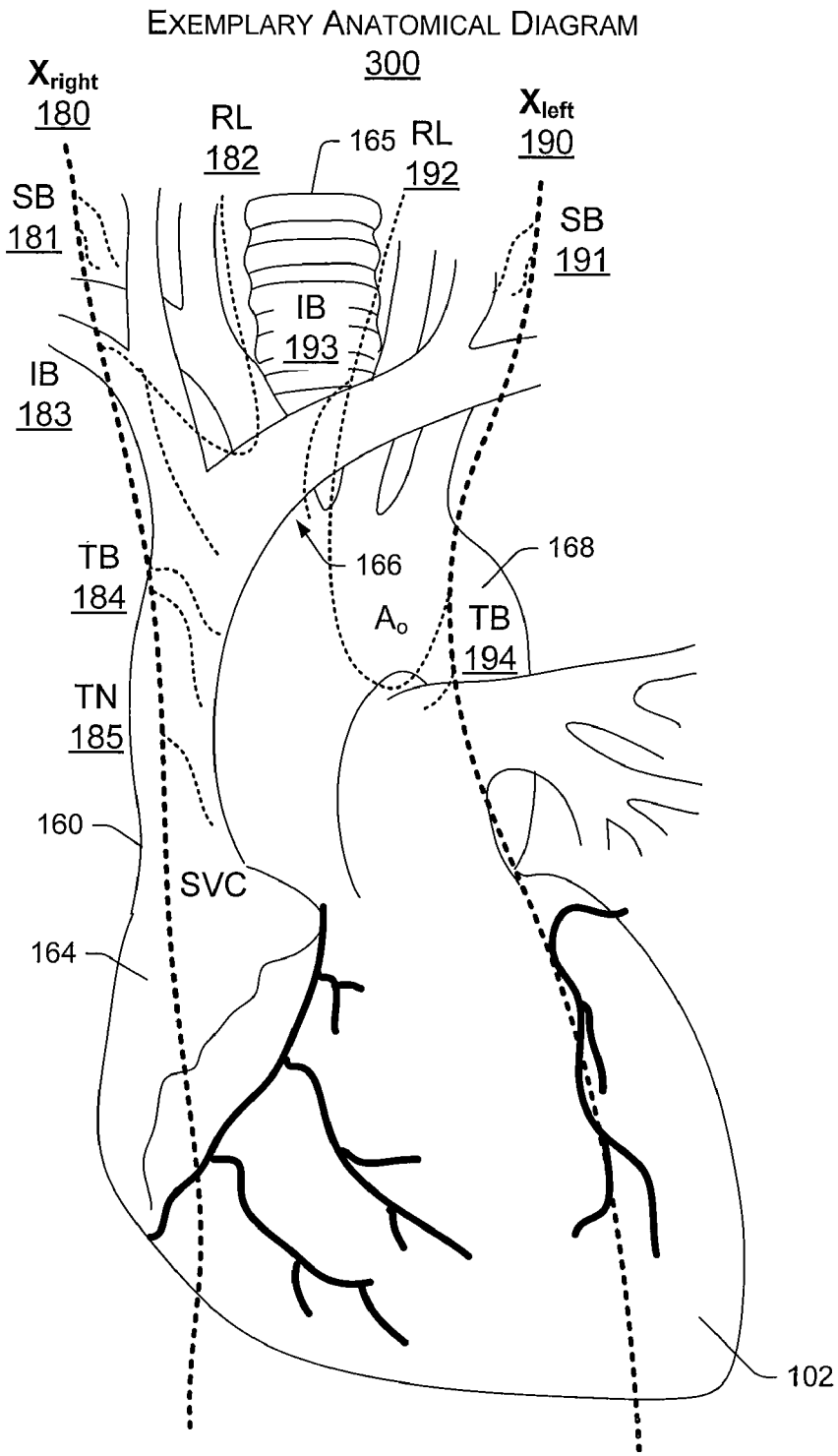
FIG. 3 is an approximate anatomical diagram that includes various autonomic nerve pathways to the heart.
Figure 4:
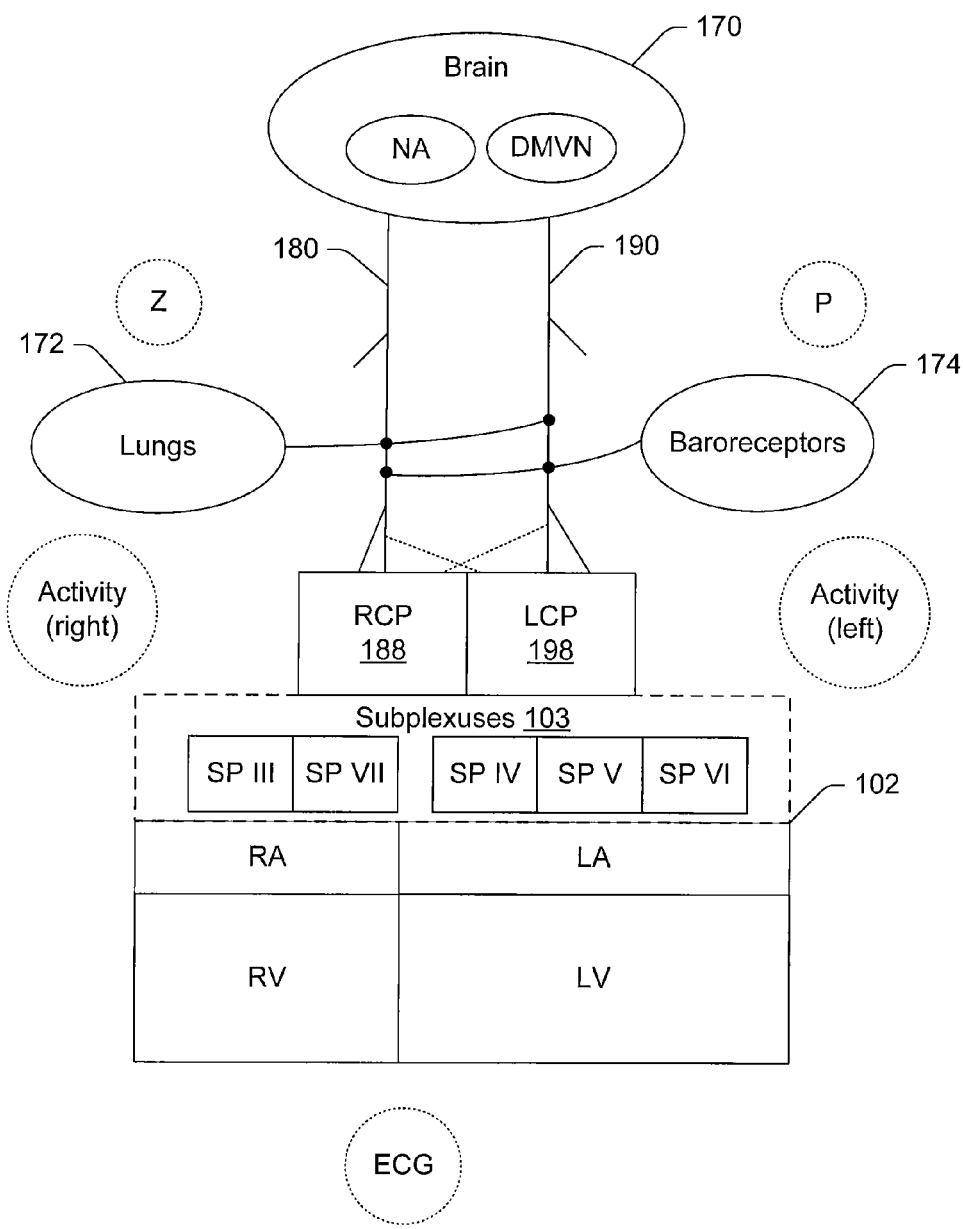
FIG. 4 is a block diagram of various autonomic nerve pathways to the heart together with other aspects of the cardiopulmonary system.

To understand better particular examples of sensing, classifying and controlling, FIG. 3 shows an approximate anatomical diagram 300 while FIG. 4 shows a more generalized block diagram of parasympathetic pathways associated with cardiac function. The pathways presented in FIGS. 3 and 4 may be used for selecting sites for sensing nerve activity and/or sites for nerve stimulating. Epicardial and/or endocardial sites for sensing and/or stimulating may be selected in part with reference to FIG. 1, 3, 4 or with reference to an article by Kawashima ("The autonomic nervous system of the human heart with special reference to its origin, course, and peripheral distribution", *Anat Embryol.* (2005) 209: 425-438)

or an article by Pauza et al. ("Morphology, distribution, and variability of the epicardiac neural ganglionated subplexuses in the human heart", *The Anatomical Record* (2000) 259(4): 353-382). Of course, for an individual patient, imaging modalities (MR, CT, etc.) may identify sites or sites may be identified through use of one or more invasive techniques (e.g., surgical, catheter, etc.).

The diagram 300 of FIG. 3 includes the heart 102, other structures (e.g., the trachea 165) and various parasympathetic, cardiac pathways. In particular, the diagram 300 illustrates the right branch 180 (XR) and the left branch 190 (XL) of the tenth cranial nerve (X) also known as the vagus nerve or vagal nerve. The vagal nerve is part of the autonomic system and regarded primarily as a parasympathetic nerve. As described in more detail below, various autonomic nerve bundles and plexuses exist that include varying degrees of a mix of parasympathetic and sympathetic nerves.

The aforementioned article by Kawashima presents various nerve pathways including parasympathetic cardiac branches arising from vagus nerve. The Kawashima article categorized vagal cardiac branches with direct connections or connections via the cardiac plexus, excluding branches of the lung or surrounding vessels and organs, as follows: superior cardiac branch (SB), which arose from the vagus nerve at about the level of the upper (proximal) portion of the recurrent laryngeal nerve branch (RL); inferior cardiac branch (IB), which arose from the recurrent laryngeal nerve branch (RL); and thoracic cardiac branch (TB), which arose from the vagus nerve at about the level of the lower (distal) portion of the recurrent laryngeal nerve branch (RL).

According to Kawashima, the cardiac plexus includes the right cardiac plexus (RCP), which usually surrounds the brachiocephalic trunk 166 (also known as the innominate artery), and the left cardiac plexus (LCP), which surrounds the aortic arch 168. On the right side, several autonomic nerves were observed passing through the dorsal, rather than the ventral, aspect of the aortic arch while, on the left side, no differences between the ventral and dorsal courses to the aortic arch were observed.

The diagram 300 shows approximate locations of some branches of the right vagus nerve 180 (SB 181; RL 182; IB 183; TB 184; TN 185) and the left vagus nerve 190 (SB 191; RL 192; IB 193; TB 194), with respect to the superior vena cava 160, the brachiocephalic trunk 166, the trachea 164 and the aortic arch 168. The dashed lines indicate that the right vagal nerve 180 and its various branches are not in the fore of the diagram 300 but rather lie generally aft (dorsal) of the SVC 160. For the left vagus nerve 190, the path courses fore (ventral) of the aortic arch 168 where a branch or branches pass underneath the arch and continue to various regions. Further the dashed lines do not indicate any particular length but rather a general course of such branches as they extend to, or around, the heart and other structures.

Kawashima reported that the superior cardiac branch (SB 181/191) was observed on the right side and the left side with one to five branches observed in each individual; that the inferior cardiac branch (IB 183/193) was also observed on the right side and the left side, with one to four branches (average of 2.1 branches; 2.4 right branches, 1.9 left branches); and that the thoracic cardiac branch (TB 184/194) was observed more so on the right side (18 subjects) compared to the left side (10 subjects), with one to five branches (average of 2.0 branches; 2.6 right branches, 1.4 left branches).

Various nerves identified in the Kawashima article extend to one or more epicardial autonomic plexuses, also referred to herein as subplexuses. The aforementioned article by Pauza et al., reports that the epicardial plexus includes seven subplexuses: (I) left coronary, (II) right coronary, (III) ventral right atrial, (IV) ventral left atrial, (V) left dorsal, (VI) middle dorsal, and (VII) dorsal right atrial. The Pauza article states that, in general, the human right atrium is innervated by two subplexuses (III, VII), the left atrium by three subplexuses (IV, V, VI), the right ventricle by one subplexus (II), and the left ventricle by three subplexuses (I, V, VI). The Pauza article also notes that diagrams from Mizeres ("The cardiac plexus in man", *Am. J. Anat.* (1963) 112:141-151), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". The Pauza article also states that the left coronary (I), right coronary (II), ventral left atrial (IV) and middle dorsal (VI) subplexuses "may be considered as being formed by the deep extrinsic plexus that receives equally from both vagi and sympathetic trunks".

Of particular note, for purposes of relating parasympathetic nerve activity and atrial activity, the right atrium is innervated by two subplexuses (III, VII) and the left atrium by three subplexuses (IV, V, VI). Further, the right subplexuses are associated predominantly with the right cardiac plexus (RCP) and the left subplexuses predominantly with the left cardiac plexus (LCP). Hence, a relationship exists between the right vagus 180, the RCP and subplexuses III and VII and a relationship exists between the left vagus 190, the LCP and subplexuses IV, V and VI.

To clarify these relationships in a more general manner, FIG. 4 shows a block diagram 400 of various autonomic pathways associated with the cardiopulmonary system. The diagram 400 includes the heart 102, subplexuses 103, the brain 170, the lungs 172, baroreceptors 174 (e.g., such as those associated with the aortic arch 168), the right vagus 180 and the left vagus 190. The right vagus 180 and the left vagus 190 communicate with the right cardiac plexus 188 (RCP) and the left cardiac plexus 198 (LCP), respectively, noting that some cross-communication may occur. In turn, the RCP 188 and the LCP 198 are in communication with the subplexuses 103, where only subplexuses specifically identified with atrial activity are shown (e.g., right atrial subplexuses III and VII and left atrial subplexuses IV, V and VI). The subplexuses are referred to as "epicardial" subplexuses, which innervate the heart 102 to some extent.

While some parasympathetic pathways may operate without direct communication to the brain 170, the brain often activates efferent pathways and receives information via afferent pathways. Thus, the brain 170 includes structures associated with cardiac vagal preganglionic neurons. In particular, two locations in the medulla oblongata associated with vagal activity are the nucleus ambiguous (NA) and the dorsal vagal motor nucleus (DVMN). A study in the rat brain (Jones, "Vagal control of the rat heart", *Experimental Physiology* (2001) 86.6, 797-801) found that neurons of the ventral group near the NA have a discharge pattern which reflects strong respiratory and baroreceptor inputs; whereas, neuronal discharge of the dorsal group near the DVMN is not modulated by either of these inputs. The DVMN group possesses C-fiber axons (conduction velocity, $<2$ m s$^{-1}$) while the NA group has B-fiber axons (conduction velocity, 10 to 30 m s$^{-1}$). Jones showed that both populations have similar functions (related to cardiac chronotropy, dromotropy and inotropy), although the magnitude and time course of the effects differed substantially and that both populations projected to clusters of ganglion cells on the atrial epicardium.

The study of Jones demonstrates that more than one type of nerve activity exists for communication along parasympathetic pathways. Further, that the specific type of activity may, by itself, identify an associated mechanism or group of mechanisms. For example, sensing of high velocity nerve activity may indicate that respiratory and/or baroreceptor mechanisms are involved. An exemplary classification method optionally relies on sensing nerve activity and determining the type of nerve activity (e.g., velocity, frequency or other characteristics) to then classify the activity as associated with risk, likelihood and/or occurrence of one or more types of atrial arrhythmias.

FIG. 4 also shows various types of information that may be acquired in addition to autonomic nerve activity, for example, electrocardiogram (ECG), impedance (Z) and pressure (P). Noting that parasympathetic pathways exist to the lungs 172 and baroreceptors 174 and that impedance information (Z) and/or pressure information (P) may aid in classifying nerve activity with respect to risk of atrial arrhythmia and/or type of atrial arrhythmia.

Various exemplary techniques optionally monitor respiratory sinus arrhythmia, for example, as an indicator of autonomic activity (or balance or tone). In general, heart rate decreases during exhalation and increases during inspiration. Changes in autonomic tone can affect the relationship between heart rate and these respiratory phases. For example, as sympathetic activity increases, the heart rate may slow less during expiration. Thus, as described herein, acquisition of information related to respiratory sinus arrhythmia may be used as an indirect technique to acquire nerve activity information (e.g., vagal nerve activity information). An exemplary method may acquire information germane to respiratory sinus arrhythmia and associate such information with risk, likelihood and/or occurrence of one or more types of atrial arrhythmias.

Figure 5:
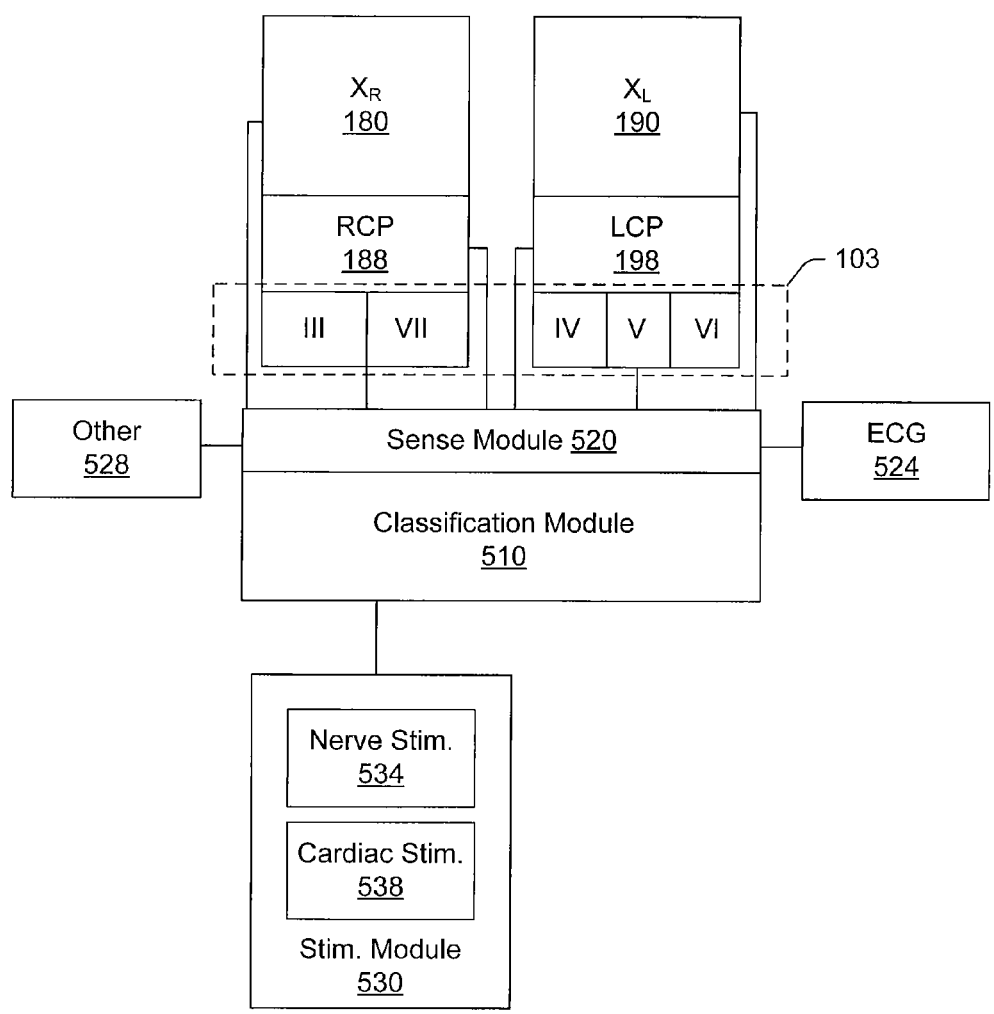
FIG. 5 is a block diagram of an exemplary classification scheme for classifying autonomic nerve activity with respect to atrial behavior.

FIG. 5 shows an exemplary classification scheme 500 for classifying nerve activity as being associated with one or more types of atrial arrhythmia. FIG. 5 also shows various parasympathetic pathways as described in FIGS. 3 and 4. The scheme 500 includes a classification module 510 that receives information from a sense module 520. The sense module 520 operates in conjunction with sensing circuitry to sense information from one or more electrodes position at an autonomic nerve. As shown in FIG. 5, the sense module may receive sensed information from one or more locations on right side and/or one or more locations on the left side. Further, the classification module 510 may control the sensing module 520 to thereby acquire additional information responsive to classification logic. For example, if the classification logic of the classification module 510 indicates that a certain risk of a particular atrial arrhythmia exists, then it may instruct the sense module to acquire additional information, optionally from another sensing site to ascertain better this risk.

The sense module 520 optionally includes features for sensing ECG information 524 and/or other information 528. In particular, ECG information 528 can be used to determine if an atrial arrhythmia exists, hence, ECG information 528 may aid in classifying nerve activity.

In the exemplary scheme 500, the classification module 510 includes a link to a stimulation module 530. The stimulation module 530 includes sub-modules for nerve stimulation 534 and for cardiac stimulation 533 (see, e.g., the device 100 of FIG. 2). Thus, classification logic may call for nerve stimulation and/or cardiac stimulation. For example, nerve stimulation may act to prevent an atrial arrhythmia, induce an atrial arrhythmia, or test a nerve pathway. Prevention, induction and testing may use stimulation to activate or block a nerve. Stimulation may also be sub-threshold with respect to the nerve or surrounding tissue. Studies indicate that sub-threshold vagal nerve stimulation can alter nerve activity. Further, stimulation may be delivered to a nerve during a refractory period of the heart (e.g., atrial or ventricular refractory period) to thereby avoid direct activation of myocardial tissue. With respect to testing, stimulation at an RCP 188 site and sensing at an epicardial subplexus site 103 may aid in understanding connectivity in a particular patient. Such connectivity may be further tested over time as a diagnostic aid. Often, changes occur in the epicardial subplexuses with aging.

The classification module 510 optionally operates using patient activity information that may indicate whether a patient is at rest, at sleep, etc. Such information may be used to trigger sensing and/or classifying or be used to aid in classifying nerve activity with respect to atrial activity.

Where the classification module 510 communicates with or instructs the stimulation module 530, the classification module 510 may include logic that varies stimulation parameters used by the stimulation module 530. Such a technique may help prevent adaptation, i.e., physiological adaptation to an applied signal.

Figure 6:
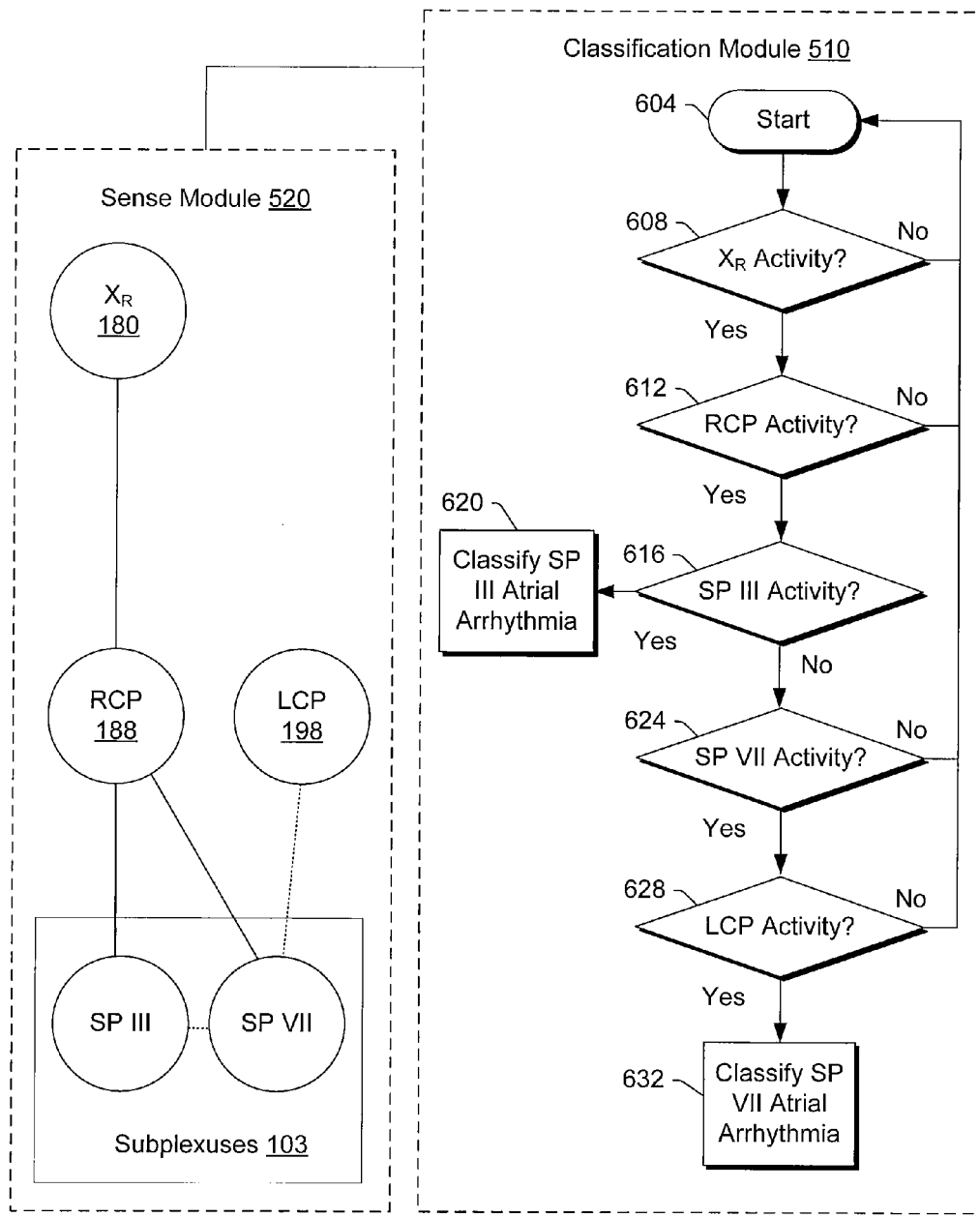
FIG. 6 is a block diagram of an exemplary classification scheme that includes classification logic for classifying autonomic nerve activity.

FIG. 6 shows an exemplary classification scheme 600 that includes the classification module 510 and the sense module 520. In this example, sensing occurs at a site on the right vagus 180 above the RCP 188, at the RCP 188, at the LCP 198, and at two subplexus 103 sites, in particular, at the SP III and at the SP VII associated with the right atrium.

Nerve activity information acquired by the sense module 520 is received by the classification module 510 to aid in classification of the nerve activity with respect to atrial behavior. The classification module 510 includes classification logic, which may be based on any of a variety of techniques. For example, "neural network" techniques may be used to classify nerve activity. As already mentioned, the classification logic may call for acquisition of more information (e.g., sensing) and/or for delivery of stimulation to a nerve or the myocardium.

In the example of FIG. 6, the classification logic of the scheme 600 corresponds to the sensing sites of the sense module 520. The logic forms a method that commences in a start block 604. A decision block 608 decides if activity exists at the right vagus site above the RCP 188. While various decision blocks refer generally to "activity", such activity may have particular characteristics (e.g., velocity, frequency, amplitude, etc.). Such characteristics, for purposes of the decision blocks, may be programmed or learned. Referring again to the decision block 608, if the activity does not include certain characteristics, upon which the decision lies, then the method continues at the start block 604. However, if such characteristics exist, then the method continues at another decision block 612.

The decision block 612 relies on information sensed at the RCP 188. Again, the decision depends on whether the sensed information includes certain characteristics. If the decision is "no", then the method continues at the start block 604. However, if the decision is "yes", then the method continues with another decision block 616. The decision block 616 renders a decision based on activity sensed at the SP III. If this activity includes certain characteristics, then the method enters a classification block 620 that classifies the activity as being associated with an SP III type of atrial arrhythmia. While an arrhythmia may not exist, the activity may nonetheless be associated with an atrial arrhythmia. For example, the activity may occur during an atrial arrhythmia and at other times as well when such an arrhythmia is not present.

If the decision block 616 decides that certain activity is not present, then the method continues in a decision block 624 that relies on sensed activity of the SP VII. If certain characteristics are present in the SP VII activity, then the method enters a decision block 628 that relies on sensed activity of the LCP 198. For example, to classify activity at the SP VII, information from the LCP 198 may be helpful. Whether the LCP 198 has a direct connection to the SP VII or not, activity at the LCP 198 may, in some instances, be associated with a certain type of atrial arrhythmia. If the decision block 628 decides that such activity exists (or, in an alternative, lack of such activity), then the method enters a classification block 632 that classifies the nerve activity as associated with a SP VII atrial arrhythmia.

Figure 7:
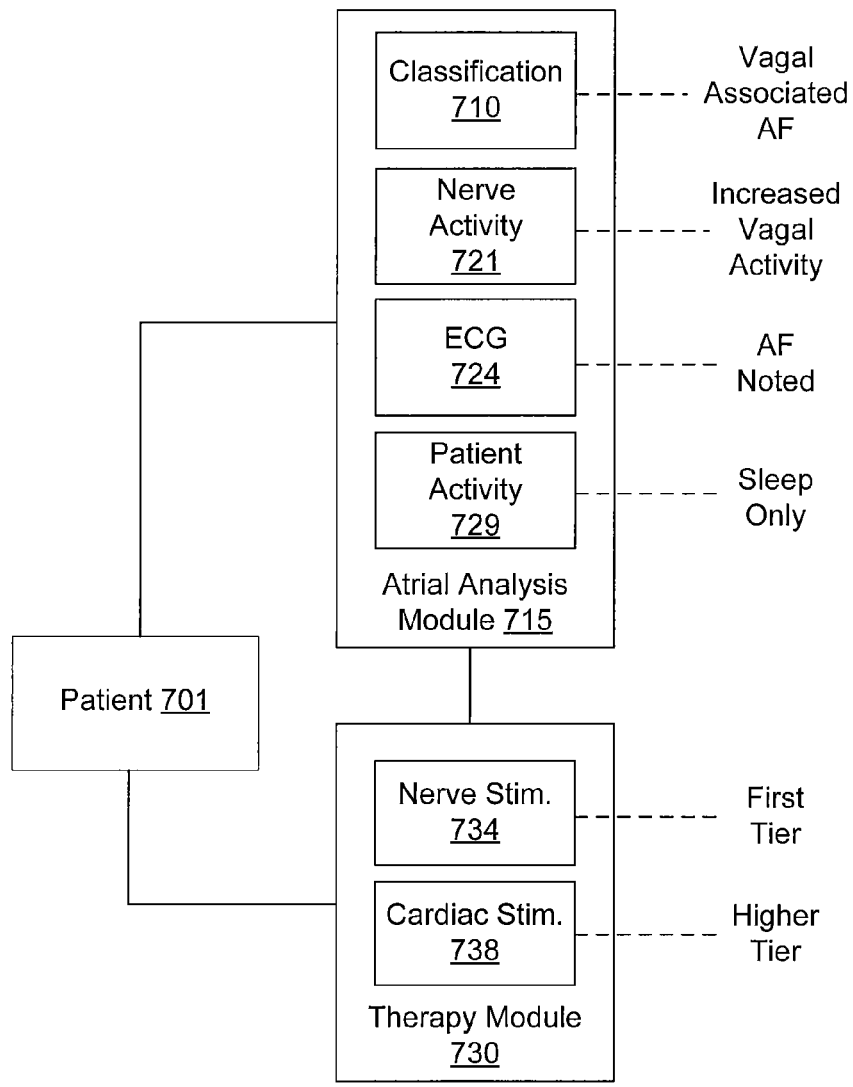
FIG. 7 is a block diagram of an exemplary learning scheme that can select and/or adjust therapy responsive to acquired information.

FIG. 7 shows an exemplary learning scheme 700 that can select and/or adjust therapy responsive to acquired information about a patient 701. An atrial analysis module 715 acquires information and analyzes the information to instruct a therapy module 730. In the example of FIG. 7, the atrial analysis module 715 includes a classification module 710, a nerve activity module 721, an ECG module 724 and a patient activity module 729 that can be used to instruct the therapy module 730, which includes a nerve stimulation module 734 and a cardiac stimulation module 738. The classification module 710 may rely on one or more types of information for purposes of classification. As described herein, the module 710 may be trained using a learning scheme and then used, for example, to call for appropriate therapy, to record atrial behavior, etc. A learning scheme may include initial and subsequent learning. Training may associate particular information with atrial behavior and then use such an association for purposes of classifying information as associated with atrial behavior (e.g., normal, abnormal, risk of arrhythmia, etc.).

The learning scheme 700 may operate by acquiring patient activity information, nerve activity information and cardiac activity information and analyzing such information with respect to atrial fibrillation (e.g., as noted by ECG information). For example, the patient activity module 729 may note that atrial fibrillation occurs when the patient 701 is asleep while the nerve activity module 721 may note an increase in vagal activity prior to onset of atrial fibrillation. The classification module 710 may then classify such patient activity and nerve activity information as being associated with a type of atrial fibrillation. Hence, upon an increase in vagal activity during sleep, the scheme 700 may classify the activity as indicative of a risk of atrial fibrillation. The classification module 710 may be further used to select an anti-atrial fibrillation therapy to prevent and/or treat sleep time atrial fibrillation for the patient 701.

In the example of FIG. 7, the anti-atrial fibrillation therapy includes a first tier that uses nerve stimulation 734 to activate or to block nerve activity and a higher tier that uses cardiac stimulation 738. For example, the atrial analysis module 715 may instruct the therapy module 730 to call for delivery of nerve stimulation 734 in an effort to prevent atrial fibrillation when the patient 701 is asleep and instruct the therapy module 730 to call for delivery of cardiac stimulation 738 in an effort to terminate atrial fibrillation occurring during sleep.

The scheme 700 may learn how anti-atrial fibrillation therapy effects patient activity, ECG, nerve activity, etc., and may adjust the therapy in response to such learning. Overall, the exemplary scheme 700 can provide classification specific therapy in a manner where therapy may be delivered where certain conditions occur (e.g., patient activity, ECG, nerve activity, etc.). Such a scheme can alleviate the need for continuous delivery of therapy, which may benefit longevity of an implanted device, enhance patient quality of life, lead to better prognosis, etc.

An exemplary method includes acquiring patient activity information, detecting one or more episodes of atrial fibrillation, based at least in part on the detecting, associating acquired patient activity information with atrial fibrillation and, upon occurrence of particular patient activity, calling for delivery of an anti-atrial fibrillation therapy to prevent and/or terminate atrial fibrillation. For example, with respect to FIG. 7, the block 729 may acquire patient activity information, the block 724 may acquire an electrocardiogram to detect one or more episodes of atrial fibrillation, the analysis module 715 may associate the patient activity information with atrial fibrillation (or optionally classify the activity per block 710) and then call for delivery of a therapy by the therapy module 730. With respect to patient activity, various techniques may be used including techniques to sense motion (e.g., accelerometer), heart rate, respiration, etc. Such a method may include acquiring vagal nerve activity and/or other information. An exemplary implantable device may include control logic to perform such a method.

An exemplary method includes acquiring vagal nerve activity information, detecting one or more episodes of atrial fibrillation, based at least in part on the detecting, associating the vagal nerve activity information with atrial fibrillation and, upon occurrence of particular nerve activity, calling for delivery of an anti-atrial fibrillation therapy to prevent and/or terminate atrial fibrillation. For example, with respect to FIG. 7, the block 721 may acquire nerve activity information, the block 724 may acquire an electrocardiogram to detect one or more episodes of atrial fibrillation, the analysis module 715 may associate the nerve activity information with atrial fibrillation (or optionally classify the activity per block 710) and then call for delivery of a therapy by the therapy module 730. Such a method may include acquiring patient activity and/or other information. For example, occurrence of a particular patient activity may initiate a call for acquisition of vagal nerve activity information. Patient activity information may also be used for purposes of calling for action (e.g., call for delivery of therapy, call for recordation of an episode, etc.). An exemplary implantable device may include control logic to perform such a method.

With respect to sensing and/or stimulating autonomic nerves, various types of electrodes exist. For example, cuff electrodes are commonly used for sensing and/or stimulating. In particular, an electrode known as a spiral cuff electrode is suitable for placement on a vagus nerve. Electrode arrays may also be used. For example, an electrode array may be configured as a cuff or a plurality of cuffs. Individual electrodes in an array or groups of electrodes in an array may be selected as appropriate through use of techniques such as the switching circuitry 226 of FIG. 2.

According to various exemplary technologies described herein, a pulse, a series of pulses, or a pulse train, can be delivered via an electrode-bearing lead portion, for example, operably connected to an implantable device to thereby activate an autonomic nerve, other nerve or tissue. The exemplary electrode-bearing lead portion may be used to selectively activate a nerve or optimally activate a nerve through its configuration and optionally through selection of and polarity of one or more electrodes.

A pulse or pulse train optionally includes pulse parameters or pulse train parameters, such as, but not limited to, frequency, pulse duration (or pulse width), number of pulses or amplitude. These parameters may have broad ranges and vary over time within any given pulse train. In general, a power level for individual pulses or pulse trains is determined based on these parameters or other parameters.

Exemplary ranges for pulse frequency for nerve or tissue stimulation include frequencies ranging from approximately 0.1 to approximately 100 Hz, and, in particular, frequencies ranging from approximately 1 Hz to approximately 20 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 2 milliseconds. Exemplary pulse amplitudes are typically given in terms of current or voltage; however, a pulse or a pulse train may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 1 V to approximately 20 V.

As described herein, various exemplary methods, devices, systems, etc., include nerve stimulation, for example, to assess atrial behavior and/or to prevent atrial arrhythmias. Depending on electrode location, stimulation parameters, etc., some risk may exist for undesirable myocardial stimulation. Undesirable myocardial stimulation generally includes stimulation that may interfere with proper operation of the heart. For example, delivery of stimulation during a vulnerable period may cause arrhythmia. To avoid undesirable myocardial stimulation and/or to reduce risk associated with any inadvertent myocardial stimulation associated with stimulation of a nerve, various exemplary methods, devices and/or systems include or can implement timing and/or pacing schemes. For example, an exemplary method includes synchronizing delivery of a nerve stimulation pulse train with the action potential refractory period of a myocardium depolarization, which may be due to a paced and/or an intrinsic event.

According to various exemplary methods, devices and/or systems described herein, and equivalents thereof, stimulation of parasympathetic nerves, other nerves and/or tissue allows for influence of cardiac activity. For example, various exemplary methods and corresponding stimulation devices rely on placement of one or more electrodes in a vessel, e.g., an epicardial vein or an epicardial venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Various exemplary methods, devices, systems, etc., may rely on placement of one or more electrodes in a non-epicardial vein. Such exemplary methods, devices, systems, etc., are optionally suitable for stimulation of parasympathetic nerves at locations, for example, generally along a parasympathetic pathway between the heart and brain. Further, other exemplary methods, devices and/or systems rely on placing one or more electrodes through the wall of a vein and proximate to a parasympathetic nerve, other nerve or tissue. Yet other exemplary methods, devices, systems, etc., rely on placing one or more electrodes proximate to a nerve without first passing the electrode through a vein or vein wall.

Another type of placement for an electrode and/or lead involves epicardial via the intrapericardial space from outside of the pericardial sac. For example, a subxyphoid incision and insertion of a needle, stick or other placement device may be made to access the pericardial sac (e.g., a process used for pericardiocentesis) and to position an electrode and/or lead. Such an electrode or lead may then be connected to an implantable device (e.g., the device 100). In some instances, a small satellite device may be implanted in the intrapericardial space where the satellite device communicates (uni or bi-directional) with another device (e.g., the implantable device 100).

CONCLUSION

Although various exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method for use in an implantable medical device implanted within a patient, said method comprising:
    training the device to distinguish between sleep time atrial fibrillation and non-sleep time atrial fibrillation by:
        acquiring patient activity information using the device, wherein the patient activity information comprises vagal nerve activity information, information sufficient to indicate if a patient is asleep and information sufficient to indicate if a patient is in an activity state other than asleep;
        acquiring patient electrocardiogram information using the device, wherein the information is sufficient to indicate if the patient is experiencing atrial fibrillation;
        upon detection of an episode of atrial fibrillation, associating the acquired vagal nerve activity information with sleep time atrial fibrillation if the acquired patient activity information indicates that the patient is asleep at the time of atrial fibrillation detection, or associating the acquired vagal nerve activity information with non-sleep time atrial fibrillation if the acquired patient activity indicates that the patient is in an activity state other than asleep at the time of atrial fibrillation detection;
    subsequent to the training, upon occurrence of sensed vagal nerve activity associated with sleep time atrial fibrillation, selecting an anti-atrial fibrillation therapy and calling for delivery of the selected anti-atrial fibrillation therapy to prevent and/or terminate atrial fibrillation classified as sleep time atrial fibrillation; and
    subsequent to the training, upon occurrence of sensed vagal nerve activity associated with non-sleep time atrial fibrillation, selecting an anti-atrial fibrillation therapy and calling for delivery of the selected anti-atrial fibrillation therapy to prevent and/or terminate atrial fibrillation classified as non-sleep time atrial fibrillation.

2. The method of claim 1 wherein the vagal activity information comprises vagal activity information acquired from the ventral right atrial nerve plexus or acquired from the dorsal right atrial nerve plexus, which are associated with the right atrium.

3. The method of claim 1 further comprising acquiring ventricular activity information.

4. The method of claim 1 further comprising classifying patient activity information with respect to risk of atrial arrhythmia.

5. The method of claim 1 wherein the called for therapy comprises nerve stimulation.

6. The method of claim 1 wherein the called for therapy comprises cardiac stimulation.

7. The method of claim 1 wherein the called for therapy comprises nerve stimulation and cardiac stimulation.

8. The method of claim 1 further comprising monitoring respiratory sinus arrhythmia as an indicator of autonomic activity or balance.

9. The method of claim 1 wherein the selected therapy comprises a nerve stimulation therapy to prevent atrial arrhythmia and comprises a cardiac stimulation therapy to terminate atrial arrhythmia.

10. The method of claim 8 wherein the associating further comprises associating autonomic activity or balance with atrial fibrillation.

* * * * *